United States Patent [19]
Mallamo et al.

[11] Patent Number: 5,134,135
[45] Date of Patent: Jul. 28, 1992

[54] ANTIANDROGENIC SULFONYLSTEROIDOOXAZOLES

[75] Inventors: John P. Mallamo, Kinderhook; Joseph R. Wetzel, Colonie, both of N.Y.

[73] Assignee: Sterling Drug Inc., New York, N.Y.

[21] Appl. No.: 541,658

[22] Filed: Jun. 21, 1990

[51] Int. Cl.$^5$ .................. C07J 51/00; A61K 31/58
[52] U.S. Cl. ................................ 514/176; 540/57
[58] Field of Search .................. 540/57, 49, 50, 56, 540/158; 514/176

[56] References Cited

U.S. PATENT DOCUMENTS 4,297,350  10/1981  Babcock et al. ............... 540/57
4,684,636  8/1987   Christiansen et al. ......... 540/57

OTHER PUBLICATIONS

Batzold, et al., Drug Development Research 21:29–35 (1990).
Kaneko, et al., Chem. Pharm. Bull. 17(1) 11–22, 1969.
Hadley, Endocrinology [Prentice-Hall Englewood, N.J. 1984] pp. 414–416.
Omar et al., Journal of Pharmaceutical Sciences, vol. 73, pp. 1871–1873, 1984.
Ibrahim et al., Journal of Heterocyclic Chemistry, vol. 19, pp. 761–768, 1982.
Wolloch et al., Tetrahedron, vol. 32, pp. 1289–1292, 1976.
Crabbë et al., Tetrahedron, vol. 27, pp. 711–725, 1971.
Ohta et al., Chemical and Pharmaceutical Bulletin, vol. 16, pp. 1487–1497, 1968.

*Primary Examiner*—Robert T. Bond
*Assistant Examiner*—E. C. Ward
*Attorney, Agent, or Firm*—Theodore C. Miller; Paul E. Dupart

[57] ABSTRACT

2'-Alkylsulfonylsteroido[2,3-d]oxazoles, for example 2'-methylsulfonyl-5α-pregn-2-en-20-yno[2,3-d]oxazol-17β-ol, which are useful as antiandrogenic agents, and proceses for preparation, method of use and compositions thereof are disclosed.

1 Claim, No Drawings

ANTIANDROGENIC SULFONYLSTEROIDOOXAZOLES

BACKGROUND OF THE INVENTION

1. Field of the Invention

The invention relates to 2'-alkylsulfonylsteroido[2,3-d]oxazoles, which are useful as antiandrogenic agents, and processes for preparation, method of use and compositions thereof.

2. Information Disclosure Statement

Christiansen et al. U.S. Pat. No. 4,684,636 issued Aug. 4, 1987 describes antiandrogenic sulfonylsteroidopyrazoles including as EXAMPLE 1 the compound having the structural formula

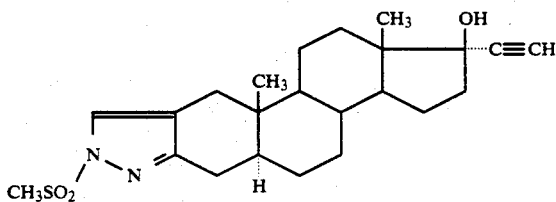

which showed relative binding affinities of 2.1 at 1 hr. and 0.09 at 18 hr. in the rat prostate androgen receptor competition assay and an $AED_{50}$ value of 14 mg./kg. orally in the test for antiandrogenic activity in the castrated immature male rat.

Babcock et al. U.S. Pat. No. 4,297,350 issued Oct. 27, 1981 describes a series of steroido[2,3-d]oxazoles having the structural formula

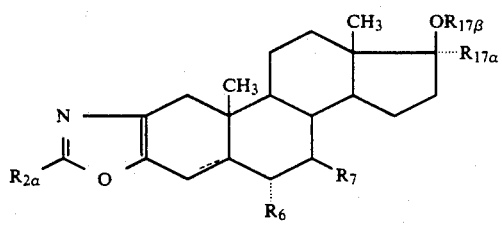

wherein $R_{2a}$ is hydrogen, alkyl of one to four carbon atoms or benzyl, $R_6$ is hydrogen or methyl, $R_7$ is hydrogen or methyl, $R_{17a}$ is hydrogen, alkyl of one to four carbon atoms, alkenyl of two to four carbon atoms or alkynyl of two to four carbon atoms, $R_{17\beta}$ is hydrogen, alkyl of one to four carbon atoms, alkenyl of two to four carbon atoms,

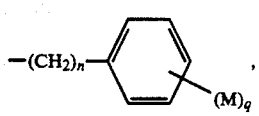

—$(CH_2)_n$—$CH(CH_2)_m$, —$CH_2$—alkenyl wherein alkenyl has two to fifteen carbon atoms or —$CH_2$—C≡CH, $R_{17a}$ and $R_{17\beta}$ can be connected to form a cyclic ether of four or five carbon atoms, M is hydrogen, methyl, methoxy, trifluoromethyl, hydroxy, nitro, fluoro, chloro or bromo, m is 4–6, n is 0–4, q is 1–2 and wherein when q is 2 the M's can be the same or different and allegedly having utility as male contraceptives.

Omar et al. (Journal of Pharmaceutical Sciences, vol. 73, pp. 1871–1873, 1984) describes the 2'-thiosteroido[2,3-d]oxazoline having the following structural formula but does not describe an biological property thereof.

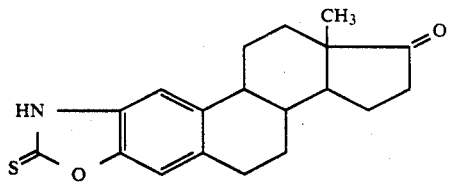

Ibrahim et al. (Journal of Heterocyclic Chemistry, vol. 19, pp. 761–768, 1982) describes a series of 2'-(substituted amino)steroido[2,3-d]oxazoles having the structural formula

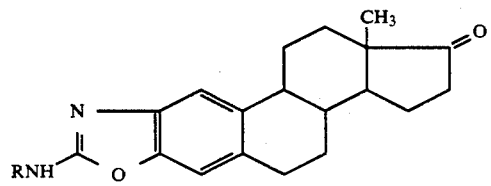

wherein R is cyclohexyl, benzyl, phenyl, 3- and 4-methylphenyl, 4-methoxyphenyl, 4-fluorophenyl, 4-chlorophenyl and 4-bromophenyl. The reference states that the compounds were tested "for in vitro anabolic-catabolic activities by measuring their effects on the activity of bovine pancreatic ribonuclease" and shown "to possess almost the same percentage activation as that induced by estrone on the enzyme".

Wolloch et al. (Tetrahedron, vol. 32, pp. 1289–1292, 1976) describes 2'-methyl-5α-cholest-2-eno[2,3-d]isoxazolebut does not describe any biological property thereof.

Crabbé et al. (Tetrahedron, vol, 27 pp. 711–725, 1971) describes 2' methyl-estra-1(10),2,4-trieno[2,3-d]oxazol-17β-ol acetate ester but does not describe any biological property thereof Ohta et al. (Chemical and Pharmaceutical Bulletin, vol, 16, pp. 1487'1497, 1968) describes 2'-methyl-5α-androst-2-eno [2,3-d]oxazol-17β-ol and the acetate ester thereof and 2'-methyl-5α-cholest-2-eno[2,3-d]oxazole. Concerning the androstane derivatives the reference states only that they "revealed considerably diminished activities when compared with testosterone propionate given by subcutaneous injection." No statement is made concerning any biological property of the cholestane derivative.

SUMMARY OF THE INVENTION

In a first composition of matter aspect the invention is a compound having the structural formula

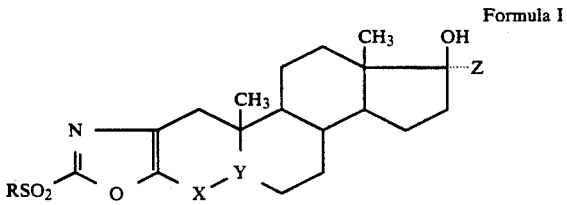

Formula I wherein
R is $CH_3$, $CH_3CH_2$, $CH_3CH_2CH_2$ or $(CH_3)_2CH$;
X-Y

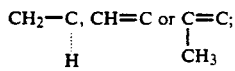

and

Z is H, CH$_3$, CH$_2$CH$_3$, C≡CH or CH=CH$_2$.

The compounds of Formula I are useful as antiandrogenic agents.

In a first process aspect the invention is the process of preparing a compound of Formula I which comprises oxidizing with a peroxide the corresponding compound having the structural formula

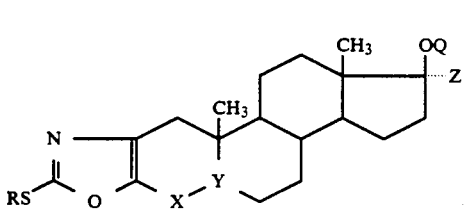

Formula II wherein Q is H; or oxidizing with a chromium oxide the corresponding compound of Formula I wherein Z is H and alkylating with the corresponding Z'-Li or Z'-MgCl or Z'-MgBr wherein Z' is CH$_3$, CH$_2$CH$_3$, C≡CH or CH=CH$_2$ the resulting compound having the structural formula

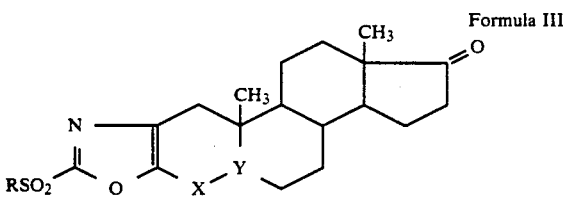

Formula III to form the corresponding compound of Formula I wherein Z is Z'; or hydrogenating with a palladium catalyst the corresponding compound of Formula I wherein Z is C≡CH to form the corresponding compound of Formula I wherein Z is CH=CH$_2$ or CH$_2$CH$_3$.

In a second process aspect the invention is the process for effecting an antiandrogenic response in a mammal which comprises administering to the mammal an antiandrogenically effective amount of a compound of Formula I.

In a second composition of matter aspect the invention is a composition which comprises an antiandrogenically effective concentration of a compound of Formula I and a pharmaceutically acceptable vehicle.

DETAILED DESCRIPTION OF THE INVENTION INCLUSIVE OF THE PREFERRED EMBODIMENTS

Preparation of the Compounds

In the preparative process aspect of the invention and the following description "corresponding" means that the variables of the reactants used to prepare a particular compound of Formula I are the same as those of the compound of Formula I.

The peroxide for oxidizing a compound of Formula II to the corresponding compound of Formula I is any peroxide capable of oxidizing RS to RSO$_2$ and is preferably a peroxyacid, most preferably potassium peroxymonosulfate (OXONE). The preferred chromium oxide for oxidizing a compound of Formula I wherein Z is H to the corresponding compound of Formula III is pyridinium chlorochromate. Alternatively the compound of Formula III is prepared by oxidizing the corresponding compound of Formula II wherein Q and Z taken together are a bond, that is wherein the 17-substituent is keto, with a peroxide, preferably potassium peroxymonosulfate (OXONE). All three oxidations are carried out in an inert solvent at a temperature in the range from 0° C. to 100° C. The preferred solvent for the potassium peroxymonosulfate oxidations is aqueous acetic acid. The preferred solvent for the pyridinium chlorochromate oxidation is dichloromethane. Alkylation of the compound of Formula III with Z'-Li Z'-MgCl or Z'-MgBr, which are known compounds, is carried out in an ethereal solvent at a temperature in the range from −100° C. to 100° C. The preferred ethereal solvent is tetrahydrofuran. The preferred palladium catalyst for hydrogenating C≡CH to CH=CH$_2$ is palladium on strontium carbonate. The preferred solvent therefor is pyridine. The preferred palladium catalyst for hydrogenating C≡CH to CH$_2$CH$_3$ is palladium on carbon. The preferred solvent therefor is ethanol. Both hydrogenations are carried out at a temperature in the range from 0° C. to 100° C.

The compound of Formula II wherein Q is H is prepared by reaction of the corresponding compound having the structural formula

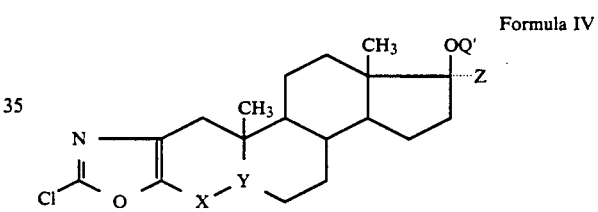

Formula IV wherein Q' is H or COCH$_3$ with the corresponding RSNa formed from RSH and sodium hydride in an inert solvent to afford the corresponding compound of Formula II wherein Q' is H or COCH$_3$. The preferred inert solvent is dimethylformamide. The reaction is carried out at a temperature in the range from −50° C. to 100° C. Q' as COCH$_3$ is removed with a strong base in an alcoholic or aqueous alcoholic solvent at a temperature in the range from −50° C. to 100° C. The preferred strong base is potassium carbonate. The preferred alcohol of the alcoholic or aqueous alcoholic solvent is methanol.

Alternatively the compound of Formula II wherein Z is Z' is prepared by alkylation of the corresponding compound of Formula II wherein Q and Z taken together are a bond (keto) with Z'-Li, Z'-MgCl or Z'-MgBr in an ethereal solvent at a temperature in the range from −100° C. to 100° C. The preferred ethereal solvent is tetrahydrofuran. The compound of Formula II wherein Q and Z taken together are a bond is prepared from the corresponding compound of Formula II wherein Q is H and Z is H by oxidation with a chromium oxide, preferably pyridinium chlorochromate, in an inert solvent at a temperature in the range from −50° C. to 100° C. The preferred inert solvent is dichloromethane. The compound of Formula IV is prepared by reaction of the corresponding compound having the structural formula

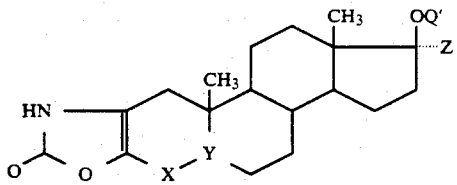

Formula V wherein Q' is H or COCH₃ with phosphorus oxychloride and phosphorus pentoxide with or without an inert solvent at a temperature in the range from 0° C. to 100° C. Since phosphorus oxychloride acts as solvent as well as reactant, the reaction is preferably carried out without an inert solvent. If an inert solvent is used, dichloromethane is preferred.

The compound of Formula V is prepared by reaction of the corresponding compound having the structural formula

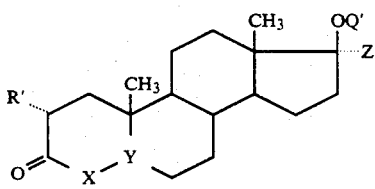

Formula VI wherein Q' is H or COCH₃ and R' is Br with potassium cyanate or sodium cyanate in an aqueous alcoholic solvent at a temperature in the range from 0° C. to 100° C. The preferred alcohol of the aqueous alcoholic solvent is ethanol.

The compounds of Formula VI wherein R' is Br are generally known or are prepared by bromination of the corresponding compounds wherein R' is H.

In the examples set forth below structures of products are inferred from structures of starting materials and expected courses of preparative reactions. Structural confirmation and estimation of purity of starting materials and products are measured by one or more of melting temperature range (m.r.), elemental analysis, infrared (IR) spectral analysis, ultraviolet (UV) spectral analysis, nuclear magnetic resonance (NMR) spectral analysis, gas chromatography (GC), high pressure liquid chromatography (HPLC) medium pressure liquid chromatography (MPLC) and thin layer chromatography (TLC).

EXAMPLE

A. Under nitrogen with stirring a solution of 17β-acetoxy2α-bromo-5α-androstan-3-one (the compound of Formula VI wherein Q' is COCH₃, R' is Br, X-Y is

and Z is H; 25 g.) and potassium cyanate (7.5 g.) in aqueous ethanol (90%, 250 ml.) was heated under reflux for 3 hours. The reaction mixture was combined with that of each of three identical reactions and the combined reaction mixtures were concentrated under reduced pressure. Chloroform was added to the residue and the solution was filtered. The filtrate was dried over magnesium sulfate, filtered and concentrated. The residual oil was crystallized from ether and the crystals were washed with hexane and a little ether affording the compound of Formula V wherein Q' is COCH₃, X-Y is

and Z is H (41 g., 45% yield), part (1 g.) of which was purified first by passage through a pad of silica gel and then by MPLC using hexaneethyl acetate (1:1) as eluant affording a white crystalline solid (410 mg., m.r. 302°–304° ). B. Under nitrogen with stirring at 0° C. the compound of Formula V wherein Q' is COCH₃, X-Y is

and Z is H (the product of part A of this example, 100 g.) was added in portions to phophorous oxychloride (1000 ml.). Phosphorous pentoxide (1 g.) was then added. Stirring was continued for 15 minutes at 0° C. then under reflux for 5 hours. More phosphorous pentoxide (1 g.) was added and refluxing was continued for 1 hour. The reaction mixture was concentrated. Chloroform was added. The resulting solution was washed twice with water and then with aqueous sodium chloride solution, dried over magnesium sulfate and potassium carbonate and concentrated under vacuum affording the compound of Formula IV wherein Q' is COCH₃, X-Y is

and Z is H as a dark oil.

C. Under nitrogen with stirring at 0° C. under a dry ice condenser methanethiol (27.1 g.) was added slowly to a suspension of sodium hydride (97%, 13.9 g.) in dimethylformamide (1000 ml.). Stirring was continued for 2 hours. A solution of the entire product of part B of this example in dimethylformamide (800 ml.) was then added during 45 minutes while the temperature was maintained at <8° C. The temperature was allowed to rise to room temperature and to remain there for three days. The reaction mixture was poured into ice-water (8 l.). The resulting mixture was filtered affording a solid and a filtrate. The filtrate was extracted three times with ether. The combined ether extracts were combined with the solid, washed with aqueous sodium chloride solution, dried over magnesium sulfate, filtered and concentrated. Crystallization of the resulting dark brown oil (120 g.) gave a brown solid in two crops, the first (39 g.) from ether and the second (2 g.) from ethyl acetate after passing the mother liquor through magnesium silicate (FLORISIL) and extracting the filter pad with ethyl acetate. A solution of part (2 g.) of the brown solid in dichloromethane was eluted through silica gel with hexane-ethyl acetate (9:1) and the eluate was purified by MPLC with the same eluant affording the compound of Formula II wherein Q is COCH₃, R is CH₃, X-Y is

and Z is H (1.2 g., 23% yield for this step and the previous step combined, m.r. 186°-188° C.).

D. Under nitrogen with stirring a solution of the compound of Formula II wherein Q is COCH₃, R is CH₃, X-Y is

and Z is H (the product of part C of this example, 3 g.) in a saturated solution of potassium carbonate in methanol (60 ml.) was heated under reflux for 4 hours then concentrated Methanol and hydrochloric acid (6N, 2 ml.) were added and the mixture was concentrated. Chloroform was added to the residue and the resulting mixture was filtered. The filtrate was dried over magnesium sulfate and stripped of chloroform. A solution of part (1.7 g.) of the resulting light yellow solid (2.2 g.) in isopropyl acetate-cyclohexane (1:1) was passed through silica gel then subjected to MPLC using the same solvent mixture as eluant. Concentration of the eluate afforded the compound of Formula II wherein Q is H, R is CH₃, X-Y is

and Z is H as an off-white crystalline solid (750 mg., 28% yield, m.r. 181.0°-182.0° ).

E. With stirring at 0° C. a solution of the compound of Formula II wherein Q is H, R is CH₃, X-Y is

and Z is H (the product of part D of this example, 39 g.) in dichloromethane (100 ml.) was added to a suspension of pyridinium chlorochromate (34.93 g.) in dichloromethane (100 ml.). After 15 minutes the temperature was allowed to rise to room temperature. More pyridinium chlorochromate (2 g.) was added after 2.5 hours. After 3 hours the reaction mixture was filtered through infusorial earth (SUPER-CEL). The filtrate was passed through magnesium silicate (FLORISIL), which was washed first with ether affording a light green solid (20 g.) and then with ethyl acetate affording a green oil (9 g.). The light green solid and green oil were combined and passed through magnesium silicate (FLORISIL) ag in using chloroform and ethyl acetate as eluant affording the compound of Formula II wherein Q and Z taken together are a double bond, R is CH₃ and X-Y is

(18.8 g., 48 % yield, m.r. 178°-179° C.).

F. Under nitrogen with stirring at −78° C. acetylene gas (first passed twice through concentrated sulfuric acid and then once through soda lime) was bubbled through dry tetrahydrofuran (400 ml.). A solution of n-butyllithium in hexane (2.3M, 91.1 ml.) was added dropwise during 45 minutes with continued acetylene bubbling. Thirty minutes thereafter a solution of the compound of Formula II wherein Q and Z taken together are a double bond, R is CH₃ and X-Y is

(the product of part E of this example, 18.8 g.) in dry tetrahydrofuran (150 ml.) was added dropwise The temperature was maintained at −78° C. for 3.5 hours and then allowed to rise to room temperature during 1 hour. Saturated aqueous ammonium chloride solution was added and the layers were separated. The aqueous layer was extracted three times with ethyl acetate. The tetrahydrofuran layer and the ethyl acetate extracts were combined, dried over magnesium sulfate and concentrated. Crystallization of the residue from etherdichloromethane gave the compound of Formula II wherein Q is H, R is CH₃, X-Y is

and Z is C≡CH as a tan solid (15 g., 75% yield). Elution of the mother liquor through magnesium silicate (FLORISIL) with ether afforded a gum (6 g ), part (1 g.) of which was purified by MPLC using hexane-ethyl acetate (7:3) as eluant and recrystallization from ether-dichloromethane affording product (60 mg.) having m.r. 206°-208° C.

G. Under nitrogen with stirring at <15° C. a solution of potassium peroxymonosulfate (OXONE, 49.5%, 141.3 g.) in water (400 ml.) was added to a solution of the compound of Formula II wherein Q is H, R is CH₃, X-Y is

and Z is C≡CH (the product of part F of this example, 14.6 g.) in acetic acid (400 ml.). The temperature was maintained at <15° C. for 1 hour and then allowed to rise to and remain at room temperature overnight. Water (2 l.) was added and stirring was continued for 1 hour. The resulting light yellow crystalline solid (12.5 g.) was collected, washed with water and dissolved in ethyl acetate. The resulting solution was washed with aqueous sodium chloride solution, dried over magnesium sulfate and stripped of ethyl acetate. A solution of the resulting yellow oil (12.5 g.) in ethyl acetate was passed through magnesium silicate (FLORISIL) with ethyl acetate (2 l.). The resulting solution was concentrated to about 0.5 l. affording as a white crystalline solid the compound of Formula I wherein Q is H, R is CH₃, X-Y is

and Z is C≡CH; 9.5 g., 60% yield, m.r. 183°–185° C.), whose Chemical Abstracts name is considered to be 2'-methylsulfonyl5α-pregn-2-en-20-yno[2,3-d]oxazol-17β-ol.

Antiandrogenic Properties of the Compounds

Utility of the compounds of Formula I as antiandrogenic agents was evaluated in the in vitro rat prostate androgen receptor competition assay. In this assay prostate glands from 24 hr. castrated adult male rats weighing approximately 250 g. were homogenized in aqueous pH 7.4 buffer containing triaziquone (10 mM), sodium molybdate (20 mM), 1,4-dithiothreitol (2.0 mM) and glycerol (10%). The homogenate was centrifuged at the equivalent of 105,000 g. for 1 hr. Aliquots of the supernatant liquid (cytosol) were incubated with methyltrienolone labelled with tritium in the 17α-methyl (5 nM final concentration) in either the absence or presence of increasing concentrations ($10^{-9}$–$10^{-5}$M) of unlabelled methyltrienolone as a reference or of a test compound for 1 hr. or overnight (approximately 18 hr.) at 4.C. Triamcinolone acetonide (1 μM) was added to the oytosol before incubation to block the low affinity binding of labelled methyltrienolone to progesterone and glucocorticoid receptors. After the 1 hr. or 18 hr. incubation period an aqueous suspension of dextran (T-70, 0.05%)-coated charcoal (1%) was added to the incubation mixture and incubation was continued for 5 min. The incubation mixture was centrifuged to remove charcoal (nonprotein)-bound labelled methyltrienolone. The supernatant was separated and its radioactivity was counted to determine the concentration of protein-bound labelled methyltrienolone. The relative binding affinity was calculated as the concentration of test compound required to reduce the concentration of protein-bound labelled methyltrienolone by 50% as a percentage relative to unlabelled methyltrienolone. Androgens including the naturally occurring testosterone and 5α-dihydrotestosterone (stanolone) and the synthetic methyltrienolone and stanozolol show high relative binding affinities and 1 hr./18 hr. relative binding affinity ratios close to unity. In general antiandrogens including flutamide and cyproterone acetate show lower relative binding affinities and 1 hr./18 hr. relative binding affinity ratios greater than 10. The product of part G of the example showed a 1 hr. relative binding affinity of 1.20, an 18 hr. relative binding affinity of 0.07 and a relative binding affinity ratio of 17, which is considered indicative of antiandrogenicity.

In the process of effecting an antiandrogenic response in a mammal the antiandrogenically effective amount of the compound of Formula I can be estimated from the foregoing test results. This aspect of the invention is contemplated to be carried out in any mammal having a disease or disorder reversible by use of an antiandrogenic agent, preferably in the human male in the treatment of benign prostatic hypertrophy or prostatic cancer or in the human female in the treatment of polycystic ovarian disease or both or in other human disease or metabolic disorder amenable to treatment with an antiandrogenic agent. It can be carried out using the compound of Formula I alone, but is preferably carried out using a composition comprising the compound of Formula I and a pharmaceutically acceptable vehicle.

The Compositions

The compositions in accordance with the second composition of matter aspect of the invention can be prepared for oral, parenteral, rectal or vaginal administration and can be in solid or liquid dosage form including capsules, tablets, suppositories, solutions, suspensions and emulsions. Conventional pharmaceutically acceptable vehicles and techniques are used in preparing these dosage forms.

We claim:

1. A compound having the structural formula

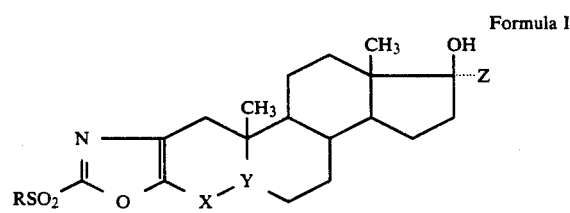

Formula I wherein
R is $CH_3$, $CH_3CH_2$, $CH_3CH_2CH_2$ or $(CH_3)_2CH$;
X-Y is $$CH_2-\underset{H}{C}, \quad CH=C \text{ or } \underset{CH_3}{C\equiv C};$$

and
Z is H, $CH_3$, $CH_2CH_3$, C≡CH or CH=$CH_2$.

2. A compound according to claim 1 wherein X-Y is

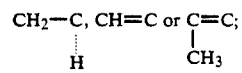

3. A compound according to claim 2 wherein R is .

4. 2'-Methylsulfonyl-5α-pregn-2-en-20-yno[2,3-d]oxazol-17β-ol according to claim 3.

5. The process for effecting an antiandrogenic response in a mammal which comprises administering to the mammal an antiandrogenically effective amount of a compound of Formula I according to claim 1.

6. The process for effecting an antiandrogenic response in a mammal which comprises administering to the mammal an antiandrogenically effective amount of a compound of Formula I according to claim 4.

7. A composition which comprises an antiandrogenically effective concentration of a compound of Formula I according to claim 1 and a pharmaceutically acceptable vehicle.

* * * * *